United States Patent [19]

Walter et al.

[11] Patent Number: 5,679,351
[45] Date of Patent: Oct. 21, 1997

US005679351A

[54] CLOVE OIL AS A PLANT FUNGICIDE

[75] Inventors: James Frederic Walter, Ashton; James Charles Locke, Silver Spring; Michele Carter Normoyle, Burtonsville, all of Md.

[73] Assignee: Thermo Trilogy Corporation, Waltham, Mass.

[21] Appl. No.: 481,858

[22] Filed: Jun. 7, 1995

[51] Int. Cl.$^6$ .................................................. A61K 35/78
[52] U.S. Cl. .................. 424/195.1; 514/558; 514/938; 514/939; 514/940; 514/941; 514/942; 514/943
[58] Field of Search ................... 424/155.1; 514/558, 514/938–943

[56] References Cited

PUBLICATIONS

Ho, et al., "Effects of Non–Polar Extracts of Clove Flower Buds on Some Life Stages of *Tribolium castaneum*," 37 *International Pest Control*, 112–113 (Jul./Aug. 1995).

Briozzo, J., et al., "Antimicrobial Activity of Clove Oil Dispersed in a Concentrated Sugar Solution," *J. App. Bact.*, 66:69–75 (1989).

Deans, S.G., and G. Ritchie, "Antibacterial Properties of Plant Essential Oils," *Intl. J. Food Microb.*, 5:165–180 (1987).

Gunathilagaraj, K., and T. Kumaraswamy, "Laboratory Evaluation of Toxicity of Clove Oil to *Callosobruchus chinensis* (L.) on Greengram Seeds," *Madras Agric.*, 65:487–488 (1978).

Kishore, N., et al., "Fungitoxic Studies with *Chenopodium ambrosioides* for Control of Damping–Off in *Phaseolus aureus* (Moong) Caused by *Rhizoctonia solani*," *Trop. Sci.*, 29:171–176 (1989).

Lawrence, B.M., "Progress in Essential Oils," *Perfumer and Flavorist*, 9:35–45 (1984).

Meena, M.R., and V. Sethi, "Antimicrobial Activity of Essential Oils from Spices," *J. Food Sci. and Technology*, 31:68–70 (1994).

Melvin, B.P., et al., "Controlling Annual Bluegrass (*Poa annua* L.) Summer Patch Disease with Faeriefungin," *HortScience*, 28:195–196 (1993).

The Merck Index, 12th ed., p. 1165, col. 1, No. 6893 1996.

Chem. Abst. 121(221:263408p, "Antifungal properties of Chinese Traditional medicinal materials", Zhang. 1994.

Chem. Abst. 114(3):20870j, "In vitro studies on antifungal activities of some aromatic oils", Thakur, et al. 1994.

Chem. Abst. 107:112501y, "Inhibitory effects of essential oil components on growth of food–contaminating fungi", Pauli, et al. 1987.

*Primary Examiner*—John W. Rollins
*Attorney, Agent, or Firm*—Quarles & Brady

[57] ABSTRACT

A clove oil formulation which inhibits soil-borne fungal diseases is disclosed. The formulation includes about 70–90% by weight rectified clove oil, and about 2–30% by weight surfactant. The surfactant includes about 15–95% by weight nonionic compounds such as ethoxylated monoglycerides, ethoxylated diglycerides, ethoxylated alcohols, silicone glycol copolymers, sorbitan fatty acid esters, ethoxylated alkyl phenols, ethylene oxide block copolymers, and propylene oxide block copolymers. The surfactant further includes about 5–85% by weight anionic compounds such as amine alkylaryl sulfonate, calcium alkylaryl sulfonate and phosphate esters. The formulation may also include up to about 30% by weight of a solvent such as alcohol, esters, glycol ethers, mineral oil, methyl esters and hydrocarbon solvents.

9 Claims, No Drawings

CLOVE OIL AS A PLANT FUNGICIDE

FIELD OF THE INVENTION

The present invention relates to a clove oil formulation which inhibits soil-borne and foliar fungal diseases such as those caused, for example, by Pythium, Rhizoctonia, Botrytis, Alternaria, Penicillium, Colletotrichum, Xanthomonas, and Fusarium.

BACKGROUND OF THE INVENTION

Most plant pathogens, notably prevalent fungal plant pathogens, are commonly controlled by the application of synthetic organic chemicals to plants in the field, either in furrow or as foliar sprays. However, as general sensitivity to synthetic chemical pesticides spreads, there is a significant desire to find "natural" substitutes for these pesticides. In the absence of effective control, however, fungal plant pathogens can extract a significant toll in plant stand, vigor, survival and yield. Some researchers have examined the effects various natural compounds have against microorganisms, most commonly to find food preservatives. For example, 50 plant essential oils, including clove oil, were tested against 25 bacteria (primarily aerobic), which might act to spoil food. The essential oils were applied both undiluted, and diluted in ethanol. The study also tested the activity of the oils based on the volatility of the oils. Among the findings of the study, both gram positive and gram negative bacterias were susceptible to clove oil. Deans et al., international Journal of Food Microbiology 5: 165–180, 1987.

In another screening study, the anti-microbial effects of spice essential oils, including clove oil, were tested. The study was performed on spoiled fruit and vegetable products by the filtered paper disk diffusion method. The results indicated that several of the essential oils studied, including clove oil, had antimicrobial activity. Meena, et al., Journal of Food Service and Technology 31(1): 68–70, 1994.

In another study of more interest to plant husbandry, an essential oil isolated from the weed *Chenopodium ambrosioides* was shown to exhibit fungicidal activity against the damping off fungus *Rhizoctonia solani*. The isolated essential oil was tested on soils, and in addition, seeds of *Phaseolus aureus* plants were soaked with the oil. The isolated essential oil was found to inhibit 44 fungi species. Kishore, et al., Trop. Sci. 29: 171–176, 1989.

The spice essential oil, clove oil, consisting primarily of the phenolic compound eugenol, has been discovered to be an effective insecticide against the cowpea weevil, a pest of stored legumes. Gunathilagaraj et al., Madras Agric. J. 54(7): 487–488, 1978. In this study, a solution of clove oil and water was either applied to weevils or poured over green gram seeds which were exposed to the insects. It was discovered that clove oil was toxic to the cowpea weevil, although the authors of the study indicated that clove oil is costly compared to other nontoxic insecticides.

Clearly, these studies indicate that some natural compounds, such as clove oil, show promise in pest control for some specific agents. However, it is difficult to generalize since compounds which are anti-bacterial or anti-insecticidal may or may not be anti-fungal and may or may not control important plant pathogens. Moreover, because clove oil is hydrophobic, it is difficult to formulate into an emulsifiable concentrate in order to produce a stable emulsion upon dilution with water, a necessary preliminary step for standard applications of plant disease control agents.

SUMMARY OF THE INVENTION

The present invention discloses a clove oil formulation which inhibits soil-borne and foliar fungal diseases. The formulation includes about 70–90% by weight rectified clove oil, and about 2–30% by weight surfactant. The surfactant includes about 15–95% by weight nonionic compounds such as ethoxylated monoglycerides, ethoxylated diglycerides, ethoxylated alcohols, silicone glycol copolymers, sorbitan fatty acid esters, ethoxylated alkyl phenols, ethylene oxide block copolymers, and propylene oxide block copolymers. The surfactant further includes about 5–85% by weight anionic compounds such as amine alkylaryl sulfonate, calcium alkylaryl sulfonate and phosphate esters. In another embodiment of the present invention, up to about 30% by weight of a solvent is included in the formulation. Examples of suitable solvents include alcohol, esters, glycol ethers, mineral oil, methyl esters and hydrocarbon solvents.

It is an object of the present invention to provide a clove oil formulation for inhibiting soil-borne fungal diseases.

It is another object of the present invention to provide a method to inhibit soil-borne fungal diseases, which method minimizes adverse side affects.

Other objects, features and advantages of the present invention will become apparent after examination of the specification and claims.

DETAILED DESCRIPTION OF THE INVENTION

The spice derivative clove oil is a natural compound which according to the literature has shown promise as an antimicrobial agent. The present invention is directed toward the use of clove oil on plants to combat plant pathogens. Clove oil formulations may be used in standard methods of application of disease control compounds, that is, soil drench and incorporation into soil prior to planting or foliar sprays, and fungal disease will be inhibited. The hydrophobic nature of clove oil, however, has made it difficult to formulate into a stable emulsion upon dilution with water. The present specification discloses that such stable emulsions can be made and used to control plant pathogenic fungi. The pathogenic fungi that can be controlled include, but are not limited to Pythium, Rhizoctonia, Botrytis, Alternaria, Penicillium, Colletotrichum, Xanthomonas, and Fusarium strains.

In the present invention, it was discovered that a special formulation of rectified clove oil and surfactant composed of ionic and anionic compounds was highly effective in inhibiting fungal diseases. The formulation, which forms a stable emulsion when diluted with water, is applied as an aqueous solution. Upon dilution, the clove water formulation is highly effective in application as a soil drench, or when incorporated into the soil prior to planting for soil-borne diseases or as a foliar spray for foliar diseases.

Rectified clove oil, the main active ingredient, consists of 84–88% v/v eugenol, 10–15% of β-caryophellene, 1–4% of α-caryophellene, together with less than 5% traces of eugenol acetate. Clove oil is denser than water, having a density in the range of 1.036 grams g/cc to 1.04 g/cc. To create the formulation of the present invention, approximately 70–90% by weight rectified clove oil is mixed with about 2–30% by weight of surfactant (preferably 10–30%) composed of about 15–95% by weight nonionic compounds, and about 5–85% by weight anionic compounds. Suitable surfactant nonionic compounds include ethoxylated monoglycerides, ethoxylated diglycerides, ethoxylated alcohols, silicone glycol copolymers, sorbitan fatty acid esters, ethoxylated alkyl phenols, ethylene oxide block copolymers, and propylene oxide block copolymers. Suitable surfactant anionic compounds include amine alkylaryl sulfonate, calcium alkylaryl sulfonate and phosphate esters. The surfactant should have a neutral pH value, and an HLB (Hydrophilic-Lipophilic Balance) value of 10 to 15. HLB value is a number between 1 and 20 assigned to emulsifiers based on the percent weight of hydrophobe to lipophobe in a molecule. The clove oil formulation is diluted with water prior to application. A preferred dilution of the formulation for application brings the rectified clove oil into the range of 0.05 to 1% by weight, and the surfactant into the range of 0.001 to 0.01% by weight.

In another embodiment of the present invention, up to 30% by weight of a solvent is included in the formulation. Examples of suitable solvents include alcohol, esters, glycol ethers, mineral oil, methyl esters, and hydrocarbon solvents.

In yet another embodiment, a formulation can contain up to 90% solvent, 7-10% clove oil and up to 3% surfactant.

The preferred embodiments of this formulation comprise 5-30% of the solvent along with 50-85% rectified clove oil and 10-30% of a surfactant blend.

It has been found that clove oil formulations are effective as inhibitors of at least some fungal plant disease organisms regardless of method of application. As described below, several important plant pathogens are effectively inhibited by clove oil formulations. Such clove oil formulations can be applied in-furrow, as soil drenches or as foliar sprays. The clove oil application results in less fungal disease as reflected by better stands of plants and more vigorous plant growth.

EXAMPLE 1

The activity of the clove oil formulation of the present invention was tested against *Rhizoctonia solani*, a soil pathogen causing damping-off of many greenhouse seedlings, including zinnia. Activity was tested by using a soilless mix infested with pathogen prior to planting of the zinnia seeds. The soilless medium was placed in a plastic bag, moistened, and infested with *R. solani*, and incubated for 2 days at 25° C. in the dark.

Zinnia seed were planted in 12×16 cm market packs with 4 rows each containing 10 seed constituting a replication with 4 replications/treatment. After planting, market packs were placed in a growth chamber at 26.5° C. with alternating 10 hours light, 14 hours dark, periods. Market packs were arranged in a randomized complete block design. Disease was assessed by recording the number of healthy seedlings in each treatment replicate 2 weeks after planting.

The clove oil formulation used in this Example had the following composition: 15 parts Witco Sponto AK 32-03, 15 parts Silwet L-77, and 70 parts rectified clove oil. The formulation was applied as an aqueous solution, at various v/v dilutions, as described below.

Treatments used were 0.25% (v/v) clove oil formulation incorporated into the soilless medium immediately prior to incubation, 0.125% (v/v) and 0.25% (v/v) clove oil applied as a drench immediately after planting, and Banrot (0.3 g product/L) applied as a drench immediately after planting.

All treatments were applied as solutions at the equivalent of 120 ml/pack. These treatments were compared against a pathogen and healthy check. After the seeded packs were watered and treatments drenched onto the surface equal amount of water were applied to move the treatment into the medium. The results are presented in Table 1.

TABLE 1

| EXPLANATION OF TREATMENT | AVR STAND COUNT | % of HEALTHY PLANTS |
|---|---|---|
| PATHOGEN ALONE | 21.3 | 58.0 |
| 0.25% CLOVE OIL INCORP INTO SOIL | 33.8 | 92.6 |
| 0.125% CLOVE OIL DRENCH | 32.7 | 89.6 |
| 0.25% CLOVE OIL DRENCH | 31.3 | 85.8 |
| BANROT DRENCH (0.3 g/L) | 34.5 | 94.5 |
| HEALTH CHECK | 36.5 | 100.0 |

These results demonstrate that the clove oil formulation of the present invention, applied as a drench at rates of 0.125% or 0.25% or incorporated at 0.25%, was efficacious in suppressing damping-off caused by *R. solani*. Seeding counts are not markedly different between the fungicide standard, Banrot, and clove oil treatments. It appears that the clove oil formulation of the present invention, used in the greenhouse, could provide a less toxic alternative to commercially available fungicides, and an alternative that may be considered more widely acceptable.

The method of this example is an effective bioassay for the efficacy of other clove oil formulations. This zinnia-Rhizoctonia bioassay can be used to determine what other clove oil formulations are effective against plant fungal pathogens.

EXAMPLE 2

This Example studied inhibition of *Botryosphaeria dothidea* mycelial growth and conidial germination by botanical extracts, insecticidal, soap and the clove oil formulation of the present invention. Mycelial inhibition and inhibition of conidial germination was evaluated in vitro for several aqueous botanical extracts (turmeric, yarrow, ginger, black pepper, pomegranate, lemongrass, basil), insecticidal soap, and the clove oil formulation. Preliminary tests indicate that the clove oil formulation of the present invention was the only one to markedly inhibit mycelial growth. The clove oil formulation used in this Example had the following composition: 15 parts Witco Sponto AK 32-03, 15 parts Silwet L-77, and 70 parts rectified clove oil. The clove oil formulation was applied as an aqueous solution, and the formulation's inhibitory activity on mycelial growth was compared at 7 concentrations of the aqueous solution between 1% and 25% (v/v dilutions).

Mycelial inhibition was measured in Petri dishes filled with potato dextrose agar by placing a 5 mm mycelial agar plug of the fungus along one edge of a dish, opposite to a 5 mm well containing sterile, distilled water (control) or 3 drops of one of the clove oil formulations. Dishes were incubated at 25° C. and colony radius was measured in all treatments when mycelial growth in the control had covered the diameter of the dish (−3 days).

The zone of mycelial inhibition was calculated as the difference between colony radius of the control and colony radius in the treatment dishes. To assess inhibition of conidial germination, test solutions were sprayed over a glass slide containing two dried water agar droplets onto which conidial extrusions from pure cultures of the fungus had been topically applied before the agar had completely solidified. Each slide was enclosed in a glass Petri dish containing moistened filter paper to maintain high humidity conditions, and dishes were incubated at 25°, 30°, or 40° C.

for 24 hr. The droplets were stained with 0.5% cotton blue in lactic acid following incubation, and germination of conidia and the condition of the germ tubes were evaluated for 60 conidia in each treatment combination.

As shown by the results presented in Table 2, the clove oil formulation of the present invention inhibited mycelial growth at 25° C. when concentrations of 6% (v/v) or higher were used. A lower concentration of clove oil (1% v/v) inhibited conidial germination completely at all temperatures tested, in contrast to the control in which germination approached 100%. Despite the high germination rate of conidia in the control treatments at all temperatures, germ tubes had ceased growing in most conidia from 30° and 40° C., suggesting that high temperature alone could inhibit germ tube extension growth. The percentage of germination at 25° and 30° C. was high for most of the botanical extracts and soap (73–97%), but germ tubes in all but the basil treatment appeared unhealthy and malformed. Germination was completely inhibited by most treatments at 40° C. As shown by the results presented in Table 3, the clove oil formulation was most active in inhibiting growth of the pathogen.

TABLE 2

| TREATMENT[1] | MYCEL INHIBITION[2] | TREATMENT | MYCEL INHIBITION |
|---|---|---|---|
| CLOVE OIL 1% | 0.00 | CLOVE OIL 12% | 2.70 |
| CLOVE OIL 3% | 0.00 | CLOVE OIL 15% | 5.00 |
| CLOVE OIL 6% | 3.30 | CLOVE OIL 25% | 4.00 |
| CLOVE OIL 9% | 2.00 | | |

[1]Means of mycelial inhibition, measured in mm from 3 Petri dishes.

TABLE 3

| TREATMENT[1] | % GERMINATION 25° C. | % GERMINATION 30° C. | % GERMINATION 40° C. |
|---|---|---|---|
| WATER | 84 | 87 | 98 |
| CLOVE OIL | 0 | 0 | 0 |
| GINGER | 73 | 30 | 67 |
| BASIL | 97 | 93 | 93 |
| BLACK PEPPER | 75 | 93 | 0 |
| POMEGRANATE | 90 | 85 | 0 |
| YARROW | 70 | 87 | 0 |
| LEMONGRASS | 77 | 80 | 0 |
| INSECTICIDAL SOAP[2] | 75 | 90 | 0 |

[1]Aqueous extracts were prepared using 30 g leaf tissue per 150 ml of water.
[2]M-Pede ™ (Mycogen Corp., San Diego, CA) at a concentration of 19.6 μl/ml water.

EXAMPLE 3

In this Example, *Rhizoctonia solani* was the pathogen studied on the host Zinnia "State Fair", using a general drench procedure. After planting seeds into infested soil, market packs were moistened lightly, and drenched, followed by 125 ml of water to move the treatments into the soilless medium. 15 parts Witco Sponto AK 32-03, 15 parts Silwet L-77, and 70 parts rectified clove oil. Drenches (125ml) were applied to each market pack containing 250 ml of soil. Banrot (8 oz/100 gal/800 sq ft)=0.3 g/L applied at 1 pt/sq ft=125 ml/market pack. Market packs were placed in a growth chamber at 25° C. for two weeks. A series of experiments were performed, with the results presented in Tables 4, 5 and 6.

1. Damping-off at 28% plant loss in pathogen treated:

TABLE 4

| TREATMENTS | AVG. HEALTHY COUNT 2-WEEKS | % CONTROL |
|---|---|---|
| Healthy | 37 | 100 |
| Rhizoctonia | 26 | 0 |
| Banrot | 34 | 72 |
| 0.18% form. Clove oil | 32 | 55 |
| 0.36% form. Clove oil | 33 | 67 |

2. Damping off at 42% plant loss in pathogen treated:

TABLE 5

| TREATMENTS | AVG. HEALTHY COUNT 2-WEEKS | % CONTROL |
|---|---|---|
| Healthy | 37 | 100 |
| Rhizoctonia | 21 | 0 |
| Banrot | 35 | 88 |
| 0.18% form. Clove oil | 33 | 80 |
| 0.36% form. Clove oil | 31 | 67 |

3. Damping-off at one week=65%, at 2 wk=88%:

TABLE 6

| TREATMENTS | AVERAGE HEALTHY COUNT 1 WEEK | % CONTROL | AVERAGE HEALTHY COUNT 2 WKS | % CONTROL |
|---|---|---|---|---|
| Healthy | 37 | 100 | 36 | 100 |
| Rhizoctonia | 14 | 0 | 4 | 0 |
| Banrot (1) | 30 | 69 | 21 | 53 |
| 0.18% form. Clove oil | 18 | 18 | 9 | 15 |
| 0.36% form. Clove oil | 29 | 65 | 20 | 50 |

(1) Two flats were not treated properly with Banrot and the stand count is low due to applicator's error.

EXAMPLE 4

In this Example, *Pythium ultimum* was the pathogen studied on the host Zinnia "State Fair", using a general drench procedure. Analogous to the procedure described in Example 3, after planting seeds and then infesting soil, market packs were moistened lightly, and drenched, followed by 125 ml of water to move the treatments into the soilless medium. The formulation used was 15 parts Witco Sponto 32-03, 15 parts Silwet L-77, and 70 parts rectified clove oil. Drenches (125 ml) were applied to each market pack containing 250 ml of soil. Banrot (8 oz/100 gal/800 sq ft)=0.3 g/L applied at 1 pt/sq ft+125 ml/market pack. Market packs were placed in a growth chamber at 18° C. for one week. Table 7 presents the results of damping off at 55.5% knockdown.

TABLE 7

| TREATMENTS | AVG. HEALTHY COUNT 2-WEEKS | CONTROL |
|---|---|---|
| Healthy | 36 | 100 |
| Rhizoctonia | 16 | 0 |
| Banrot | 35 | 95 |
| 0.18% form. Clove oil | 33 | 85 |
| 0.36% form. Clove oil | 31 | 75 |

The results of Examples 3 and 4, as presented in Tables 6 and 7, clearly indicate that the clove oil formulation of the present invention is active against two soil pathogens (Pythium and Rhizoctonia) in plant bioassays. Clove oil formulation treatments increased zinnia stands over the pathogen check and work near to or as well as the commercial fungicide, Banrot.

EXAMPLE 5

In this Example, *Uromyces appendiculatus* was the pathogen studied on the host, pinto bean (Phaseolus vulgaris cv. Pinto).

Propagation: Bean seed plants approximately 1.3 cm deep in moist potting soil at 4 seed/10cm pots were covered with black plastic on a greenhouse bench at 24° C. for 2-3 days to germinate the bean seedlings. Pots were thinned to the three most uniform plants/pot when the first trifoliate was approximately ½ expanded.

Treatment: Treatments of the clove oil formulation, in aqueous solution, 10 parts Witco Sponto AK 32-03, 5 parts Ethylene Glycol n-Butyl Ether, and 85 parts rectified clove oil (all w/w), were applied to the lower and upper primary leaf surfaces using a handheld, pump-type sprayer. The treatment was allowed to dry before inoculation with the pathogen.

Inoculation: An urediniospore suspension (20,000 spores/ml) of the *U. appendiculatus* was prepared in water containing one drop of Tween 20/liter. The suspension was agitated constantly on a stir plate using a spin bar until the spores were wetted and evenly dispersed. The suspension was then atomized onto the lower leaf surfaces only using a Crown Spra-Tool aerosol sprayer. The inoculum was allowed to dry before placing the plants into a dew chamber for a 16 hr. Infection period at 18°-21° C. The plants were removed to a warm greenhouse (min. 21° C. night temp.) to allow rust pustule development.

Disease assessment: The plants were rated for disease 7-8 days after inoculation by assessing the number of rust pustules/10cm$^2$. The results, presented in Table 8, clearly indicate that the clove oil formulation of the present invention reduces the number of bean rust pustules per leaf.

TABLE 8

| TREATMENTS | PRE-TREATMENTS | POST-TREATMENTS |
|---|---|---|
| Pathogen alone | 2.6(a) | 2.9 |
| 0.36% Clove oil | 0.7 | 3.5 |
| (Treatment was not phytotoxic) | | |
| 0.18% Clove Oil | 1.2 | 3.1 |
| 0.09% Clove Oil | 1.2 | 3.1 |
| 0.04% Clove Oil | 1.0 | 3.1 |
| 0.02% Clove Oil | 1.7 | 3.4 |

(a) These numbers denoting the number of rust pustules/cm$^2$ were obtained using a visual rating scale from (0–7), where 0 = no pustules/cm$^2$, 1 = less than 2 pustules/cm$^2$, 2 = approximately 4 pustules/cm$^2$, 3 = approximately 7 pustules/cm$^2$ and 4 = approximately 18 pustules/cm$^2$, and so on.

The activity of the clove oil formulation of the present invention against bean rust appears to be prior to inoculation only. Formulated clove oil applied at 0.36% exhibits good control of bean rust. Formulated clove oil at 0.36% was not phytotoxic in the test above.

EXAMPLE 6

The volatile activity of the clove oil formulation of the present invention was tested by dipping filter paper disks into an aqueous solution of 25% (v/v) clove oil formulation. The filter paper disk was then placed on the underside of the lid of the petri plate and a 3 mm plug of each test fungus was placed on potato dextrose agar at the edge of the plate. Plates were inverted and incubated at 25° C. in the dark as many as 10 days depending on the growth rate of the fungus. Test fungi were *Pythium ultimum*, *Rhizoctonia solani*, *Botrytis cinerea*, and *Fusarium roseum*.

Measurements were obtained over time by measuring mycelial growth. Measurements began 2 days after the mycelial plugs were placed onto the agar surface. The zone of inhibition was calculated by taking the difference between the mycelial growth of the control plate and the treated plate. Data indicated that the rate and inhibition of fungal growth was affected by the volatile activity of the clove oil formulation applied at a rate of 25%. The rate of fungal growth in the treated plate was greatly delayed as compared to the control plate for all fungi tested. Zones of inhibition for each fungus is as follows: *P. ultimum*, 34 mm; *R. solani*, 40 mm; *B. cinerea*, 39 mm; and *F. roseum*, 34 mm.

What is claimed is:

1. A method for inhibiting soil-borne fungal diseases, the method comprising incorporating into soil, prior to planting, an aqueous solution of a clove oil formulation comprising
   a. about 70–90% by weight rectified clove oil; and
   b. about 2–30% by weight surfactant comprising about 15–95% by weight nonionic compounds, and about 5–85% by weight anionic compounds, wherein fungal disease is inhibited in a subsequently planted plant and wherein the plant remains healthy.

2. The method described in claim 1 wherein the nonionic compounds are selected from the group consisting of ethoxylated monoglycerides, ethoxylated diglycerides, ethoxylated alcohols, silicone glycol copolymers, sorbitan fatty acid esters, ethoxylated alkyl phenols, ethylene oxide block copolymers, and propylene oxide block copolymers, and the anionic compounds are selected from the group consisting of amine alkylaryl sulfonate, calcium alkylaryl sulfonate and phosphate esters.

3. The method described in claim 1 wherein the clove oil formulation further comprises up to 30% by weight of a solvent selected from the group consisting of alcohol, esters, glycol ethers, mineral oil, and hydrocarbon solvents.

4. A method for inhibiting soil-borne fungal diseases, the method comprising drenching plants susceptible to said fungal diseases with a clove oil formulation comprising about 70–90% by weight rectified clove oil; and about 2–30% surfactant comprising about 15–95% by weight nonionic compounds and about 5–85% by weight anionic compounds, wherein, after the drenching step, the plant remains healthy.

5. The method described in claim 4 wherein the nonionic compounds are selected from the group consisting of ethoxylated monoglycerides, ethoxylated diglycerides, ethoxylated alcohols, silicone glycol copolymers, sorbitan fatty acid esters, ethoxylated alkyl phenols, ethylene oxide block copolymers, and propylene oxide block copolymers, and the anionic compounds are selected from the group consisting of amine alkylaryl sulfonate, calcium alkylaryl sulfonate and phosphate esters.

6. The method described in claim 4 wherein the clove oil formulation further comprises up to 30% by weight of a solvent selected from the group consisting of alcohol, esters, glycol ethers, mineral oil, methyl esters and hydrocarbon solvents.

7. A clove oil formulation for inhibiting fungal diseases in a plant, the formulation comprising:
   a. about 70–90% by weight rectified clove oil; and
   b. about 2–30% by weight surfactant comprising about 15–95% by weight nonionic compounds and about 5–85% by weight anionic compounds, wherein the formulation is not phytotoxic.

8. The clove oil formulation described in claim 7 wherein the nonionic compounds are selected from the group consisting of ethoxylated monoglycerides, ethoxylated diglycerides, ethoxylated alcohols, silicone glycol copolymers, sorbitan fatty acid esters, ethoxylated alkyl phenols, ethylene oxide block copolymers, and propylene oxide block copolymers, and the anionic compounds are selected from the group consisting of amine alkylaryl sulfonate, calcium alkylaryl sulfonate and phosphate esters.

9. The clove oil formulation described in claim 7, further comprising up to 30% by weight of a solvent selected from the group consisting of alcohol, esters, glycol ethers, mineral oil, methyl esters and hydrocarbon solvents.

* * * * *